United States Patent [19]

Couvillion

[11] 4,440,956
[45] Apr. 3, 1984

[54] SELECTIVE HYDROGENATION OF ACETYLENES IN THE PRESENCE OF BUTADIENE AND CATALYST USED IN THE HYDROGENATION

[75] Inventor: Mark C. Couvillion, Freeport, Tex.

[73] Assignee: The Dow Chemical Company, Midland, Mich.

[21] Appl. No.: 473,293

[22] Filed: Mar. 8, 1983

Related U.S. Application Data

[63] Continuation-in-part of Ser. No. 436,250, Oct. 25, 1982, abandoned, which is a continuation-in-part of Ser. No. 299,688, Sep. 8, 1981, abandoned.

[51] Int. Cl.$^3$ .................. B01J 23/68; B01J 23/72; B01J 23/84; B01J 23/86
[52] U.S. Cl. .................. 585/260; 502/318; 502/322; 502/324; 502/332; 502/334; 502/335; 502/348; 585/845
[58] Field of Search .............. 252/463, 465, 466 J, 252/466 PT; 585/260, 261, 845

[56] References Cited

U.S. PATENT DOCUMENTS 3,912,789 10/1975 Frevel et al. .................. 585/260
4,101,451 7/1978 Frevel et al. .................. 252/465

OTHER PUBLICATIONS

Above References A and B Were Cited in Grandparent Application Ser. No. 299,688.

*Primary Examiner*—W. J. Shine
*Attorney, Agent, or Firm*—G. R. Baker

[57] ABSTRACT

An improved catalyst for removal of acetylenes from liquid hydrocarbon streams with a minimum loss of diolefinic unsaturation present in said liquid composition is disclosed. The catalytic materials, basically copper metal associated with one or more activator metals are impregnated on a gamma alumina support prepared from an organo aluminum compound. The support has properties not found in alumina prepared from naturally occurring precursors.

6 Claims, 21 Drawing Figures

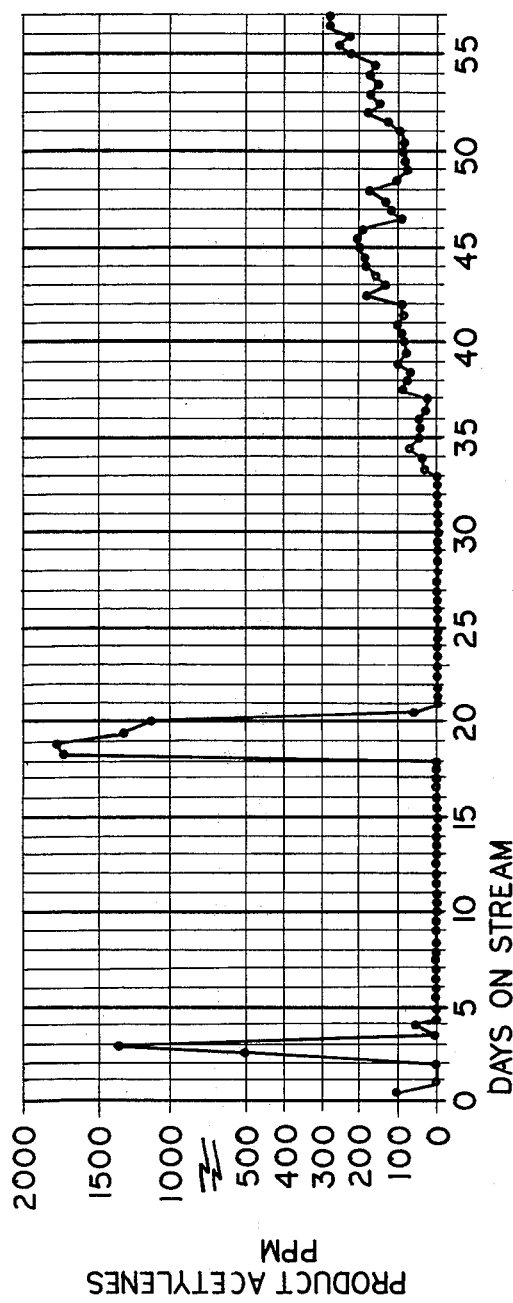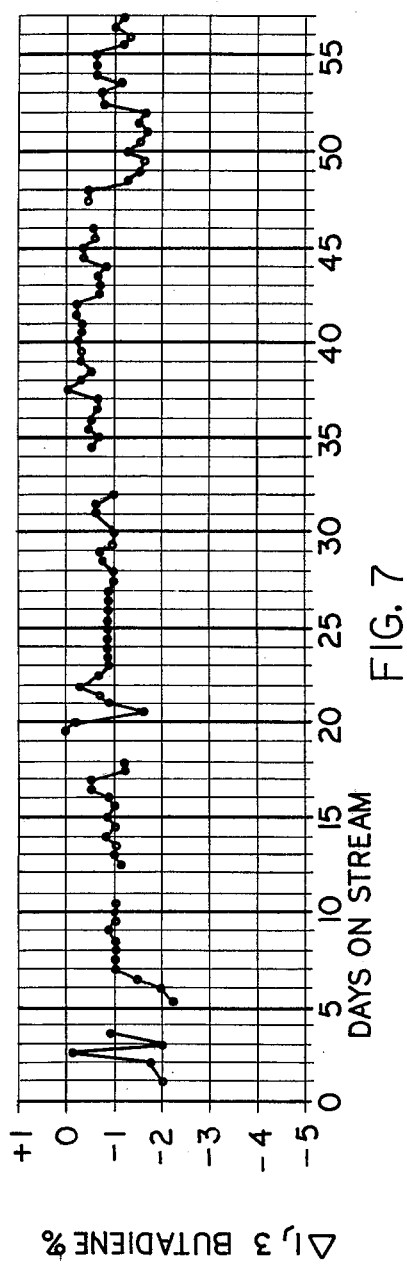
FIG. 7

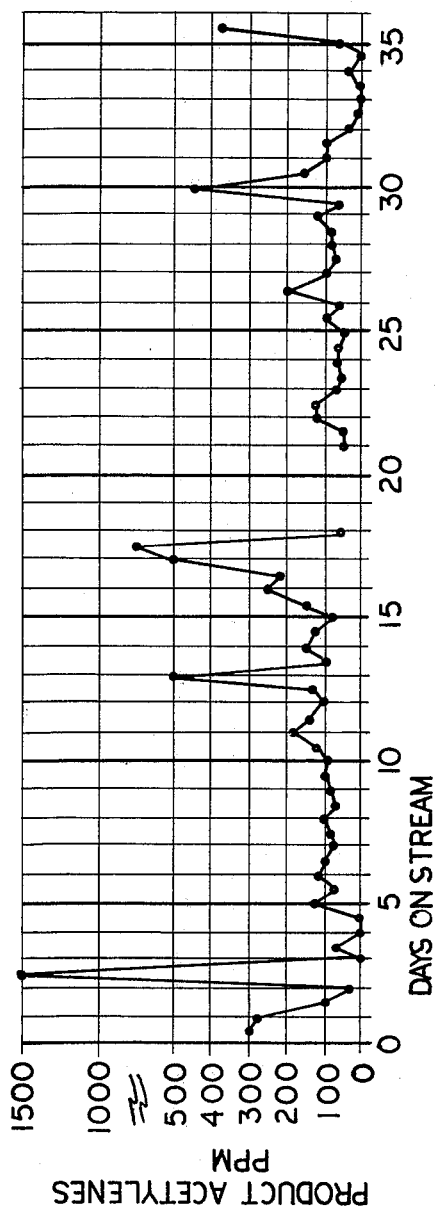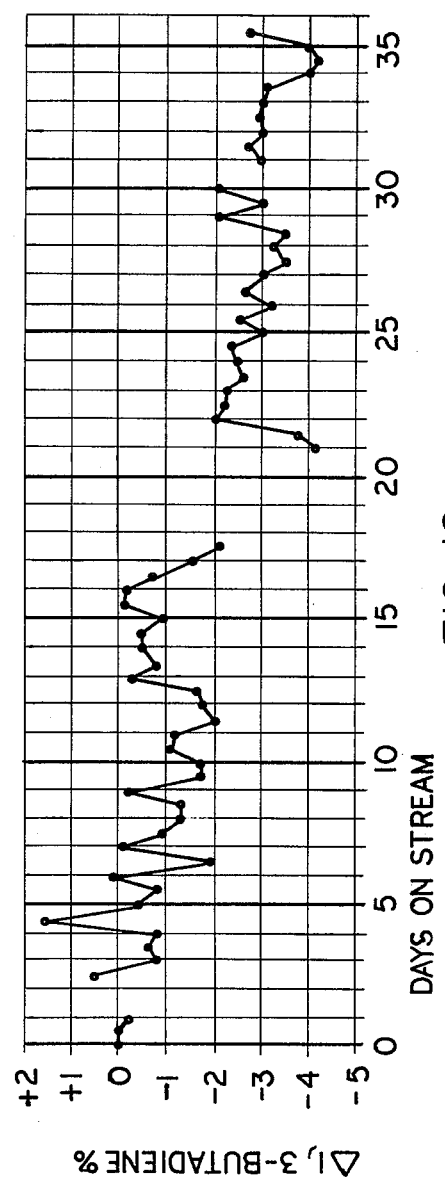
FIG. 12

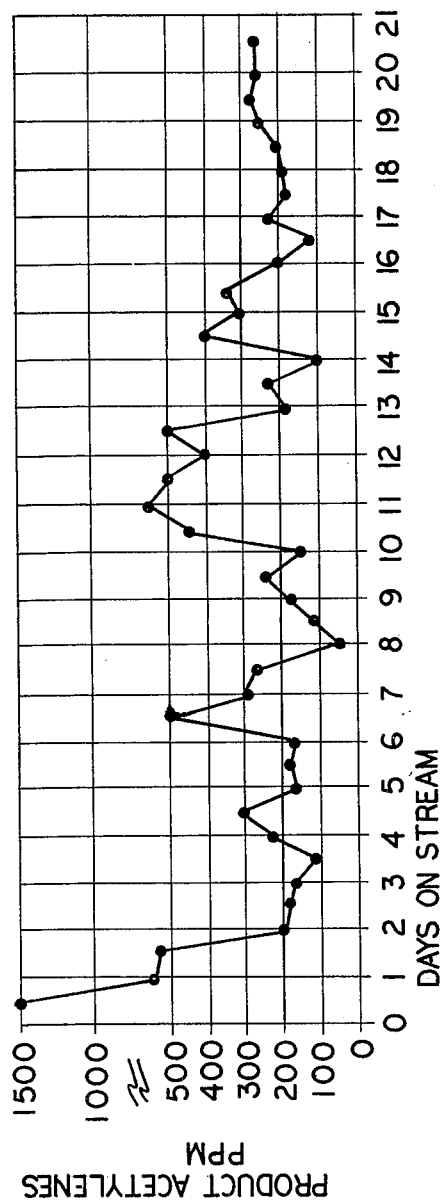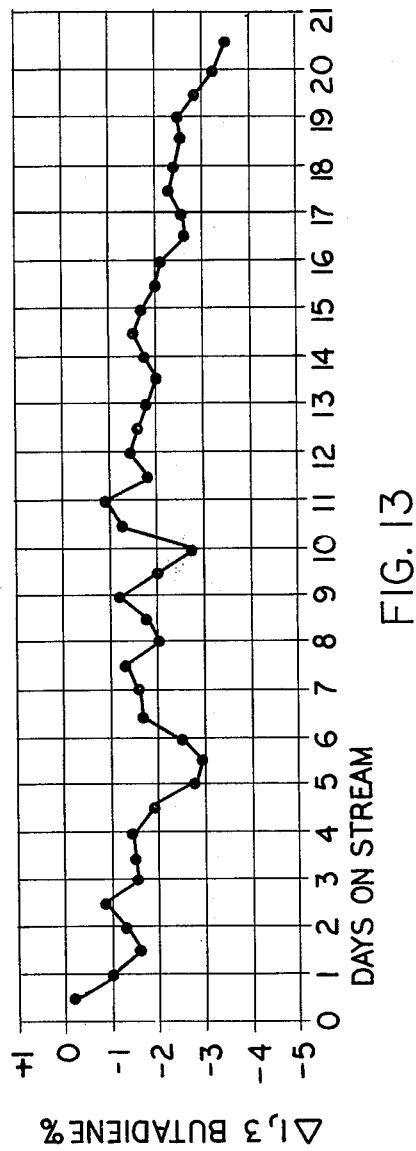
FIG. 13

SAMPLE NUMBER, SAMPLE TREATMENT, AND $\frac{R_{X-RAY}}{R_{ESCA}}$

4,440,956

SELECTIVE HYDROGENATION OF ACETYLENES IN THE PRESENCE OF BUTADIENE AND CATALYST USED IN THE HYDROGENATION

CROSS REFERENCE TO RELATED APPLICATION

This application is a continuation-in-part of my earlier filed application Ser. No. 436,250 filed Oct. 25, 1982, now abandoned, which was a continuation-in-part of application Ser. No. 299,688 filed Sept. 8, 1981, now abandoned.

BACKGROUND OF THE INVENTION

Copper metal, activated with one or more of the metals silver, platinum, palladium, manganese, cobalt, nickel, chromium and/or molybdenum on an alumina support, is well known as a catalyst for hydrogenation of acetylenes. Frevel et al. have issued several patents in which improved results are obtained (improved selectivity of hydrogenation of the acetylenic bonds in the presence of diolefinic bonding) by increasing the sodium content of the activated catalyst, U.S. Pat. No. 4,101,451, and/or high sodium oxide alumina, U.S. Pat. No. 3,912,789. However, these catalysts still hydrogenate some considerable amount of the diolefin components of such streams. As the diolefin content of these streams becomes more valuable it would be advantageous to reduce the hydrogenation of these diolefins (particularly butadiene) without also reducing the hydrogenation of the α-acetylenes.

BRIEF DESCRIPTION OF THE INVENTION

It has now been found that by employing a gamma alumina containing 35 percent by weight or less of alpha alumina and preferably a special grade of gamma alumina ($\gamma$-$Al_2O_3$), one which has low, less than 0.15 weight percent each of silicone as $SiO_2$ and sodium as $Na_2O$, less than 0.01 weight percent sulfur and less than 0.06 weight percent iron as $Fe_2O_3$, and additionally has a surface area of between about 68 and 350 square meters per gram and 90 to 60 percent of the pores have a pore diameter between about 40 Å and 120 Å and not more than 25 percent nor less than 2 percent have a pore diameter between 1000 Å to 10,000 Å, produces a catalyst support which when coated with copper (3–13 percent based on the support) and at least one activator metal permits reaching lower acetylene levels with less butadiene loss than prior art catalysts and additionally can be effectively regenerated to 90 plus percent activity over several cycles.

It has also been found that during use the gamma alumina described above undergoes a phase change, probably due to thermal treatment during operation and regeneration. Thus, a gamma alumina within the scope above defined will undergo a gradual change, as for example, during a nine month, thirteen cycle (with regeneration) run, to analyze about 35 percent alpha alumina with an attendant reduction in surface area from about 165 square meters per gram to about 68 square meters per gram. There is also a change in the pore volume distribution associated with the reduction in surface area and presence of the alpha alumina. However, the pore sizes remain within the aforedefined range. Thus, while it is preferred to start with a relative high purity gamma alumina having the above described properties and physical characteristics, it is to be understood that a carrier or support may be a combined unitary alumina consisting of a high purity alumina as above defined but having up to fifty percent alpha alumina in admixture with gamma alumina. Such a support can be readily obtained by thermal treatment of gamma alumina of the requisite purity in the presence of cuprous oxide. The phase change apparently occurs during the oxidation and/or reduction during regeneration. Presumably the cuprous oxide acts as a seed to effectuate the phase change from gamma to alpha state. However, no specific theory based on scientific data of how such a change occurs can yet be set forth. While the aforestated procedure appears to effect the change, other methods may be available from those skilled in the art of alumina production.

The catalyst carrier or support which appears to be critical or at least preferred to obtaining the aforesaid results is a special grade of gamma alumina ($\gamma$-$Al_2O_3$) prepared by decomposing trialkyl alumina to alpha aluminum monohydrate then calcining the alpha aluminum monohydrate to gamma alumina. This process produces a grade of gamma alumina normally not obtainable from naturally occuring aluminum containing ores and which has, when pressed or extruded into pellets, a higher purity than naturally occurring alumina, and a pore size and pore size distribution sufficiently different from that obtainable using naturally occurring aluminas and converting them to gamma alumina. The most ready source of catalyst support size pellets is from The Harshaw Chemicals Co. sold as 3438T, Norton Company as SA6173 and Calcicat Division, Mallinckrodt Chemical Works as CALCICAT Type A and AA. Although Conoco Chemicals Division, Conoco, Inc., manufactures a powder, CATAPAL type SB which has been found suitable and is believed to be the precursor powder for the three pellet producers, pellets produced by Conoco are not readily available except through the three pelletizers.

BRIEF DESCRIPTION OF THE DRAWINGS

The drawings, FIGS. 1–9 and 16–21 illustrate the results of the several experiments employing different supports as carriers for the catalytically active components, with respect to the acetylenes in the product stream and the loss of 1,3-butadiene from the feed stream as a result of the proces. FIGS. 12 and 13 illustrate the results obtained when the heretofore conventional support, $\gamma$-AlOOH, REYNOLDS RA-1 is employed. FIG. 21 illustrates the effect of water vapor on copper crystallite size and, in conjunction with example 8, the results of such growth on catalyst activity.

DETAILED DESCRIPTION OF THE INVENTION

EXAMPLE 1

In accordance with the present invention 300 grams of $\gamma$-$Al_2O_3$ obtained from Conoco Chemicals Division, Conoco, Inc., as ⅛" diameter by ¼" long pellets identified as CATAPAL SB had the following properties:

x-ray diffraction pattern matches Joint Committee on Powder Diffraction standards #29–63

| | |
|---|---|
| % $Na_2O$ | 0.004 |
| Sulfur | 0.01 |

| | |
|---|---|
| % SiO$_2$ | 0.008 |
| % Fe$_2$O$_3$ | 0.005 |
| Surface area (m$^2$/g) | 241 |
| Pore volume (cc/g) | 0.57 |
| Bulk density (g/cc) | 0.79 |

75% of its pores were less than 75 Å
82% of its pores were less than 100 Å
18% of the pores were between 102 Å and 8390 Å
The unburdened support was impregnated with a solution consisting of:

| | Grams | Parts By Weight |
|---|---|---|
| Cu(NO$_3$)$_2$.2½H$_2$O | 113 | 0.9135 |
| Ni(NO$_3$)$_2$.6H$_2$O | 4 | 0.0323 |
| H$_2$O | ~40 | |
| HNO$_3$ | 59 | |
| Mn(NO$_3$)$_2$ 50% solution | 3.1 | 0.0250 |
| AgNO$_3$ | 0.2 | 0.0016 |
| Cr(NO$_3$)$_3$.9H$_2$O | 1.7 | 0.0137 |
| Co(NO$_3$)$_2$.6H$_2$O | 1.7 | 0.0137 | in sufficient water of a pH of 6.5–7.5 to wet the surface of said support. Solubilization of the numerous metal salts was obtained by gentle heating. The resulting solution was poured over 300 grams of the support in a beaker while stirring to obtain even distribution. When all of the solution had been sorbed, the support was dried over night at 110° C., then calcined at 400° C. for about 6 hours.

The catalyst was loaded to a depth of about 12 inches at the middle of a laboratory 1 inch diameter by 36 inch long reactor. The remaining space of the reactor, above and below the catalyst, was filled with raschig rings. The catalyst was reduced over night with hydrogen at between 300° to 350° C. In the morning the temperature recording from several thermocouples in the bed showed an exotherm had passed up the column during the night signifying reduction of the metal oxides to their metal state. The reactor was cooled to ambient temperature and hydrogen and a liquid hydrocarbon stream having about 61% by weight 1,3-butadiene and 8716 ppm acetylenes was fed to the reactor. The reactor conditions were:

| | |
|---|---|
| Feed | 300 cc/hour |
| Recycle | 600 cc/hour |
| H$_2$ Flow | 2.8 liters/hr at atm. STP |
| H$_2$:C≡ ratio | 4:1 |
| Inlet temperature of liquid | 60° C. |
| T at thermocouple | |
| #1 ca. | 70° C. |
| #2 ca. | 67° C. |
| #3 ca. | 66° C. |
| #4 ca. | 62° C. |
| #5 ca. | 58° C. |

Regeneration was accomplished by purging the reactor with N$_2$ at about 12 liters/min., followed by introduction of air first at 18.15 liters/min. then 13.3 liters/min. Finally the air was shut off and H$_2$ was admitted at 4.1 liters/min. The GHSV were: N$_2$ 1650 hr$^{-1}$, N$_2$+air (max.) 3460 hr$^{-1}$; and, N$_2$+H$_2$ 2215 hr$^{-1}$, respectively.

Figure 1:
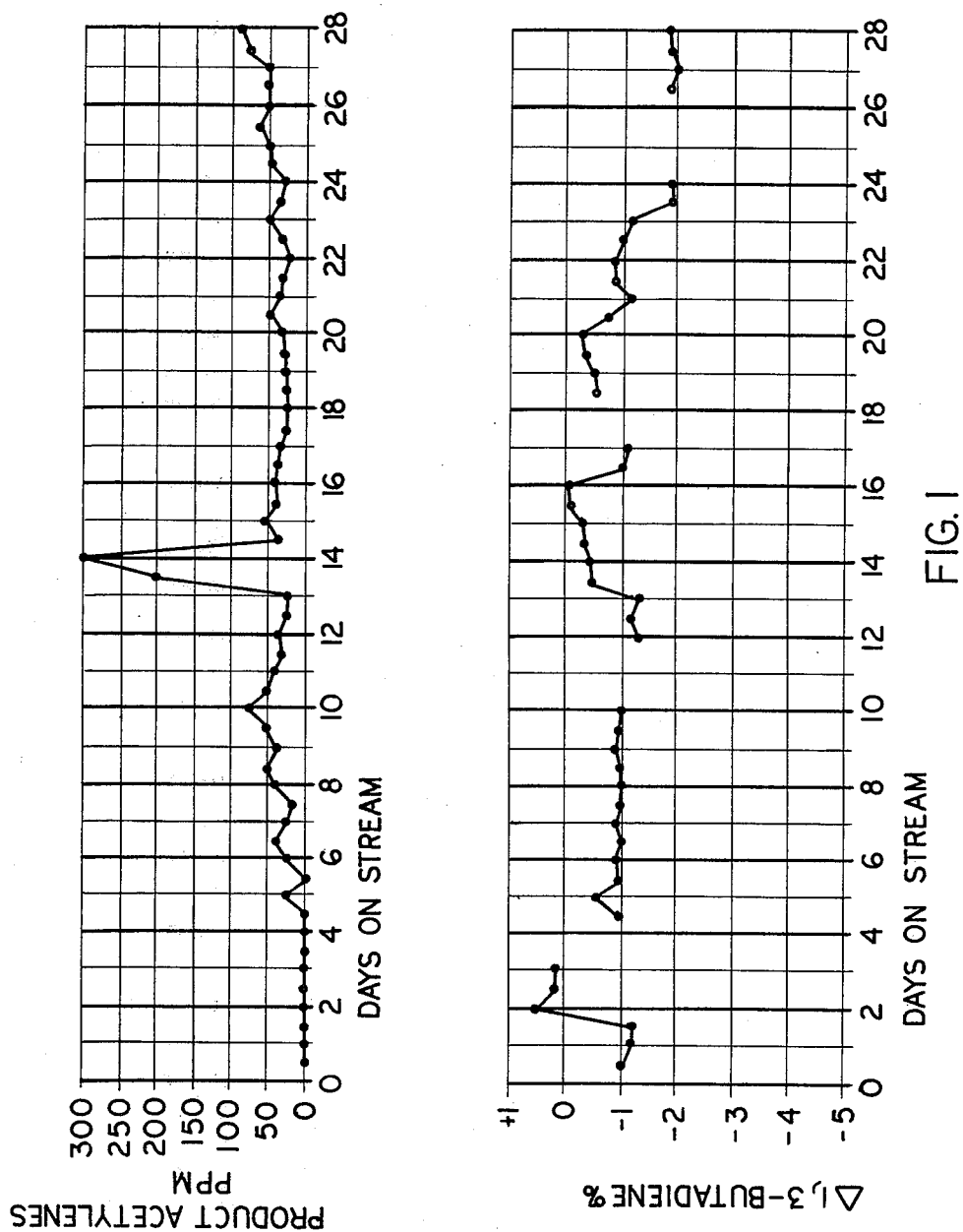
Figure 2:
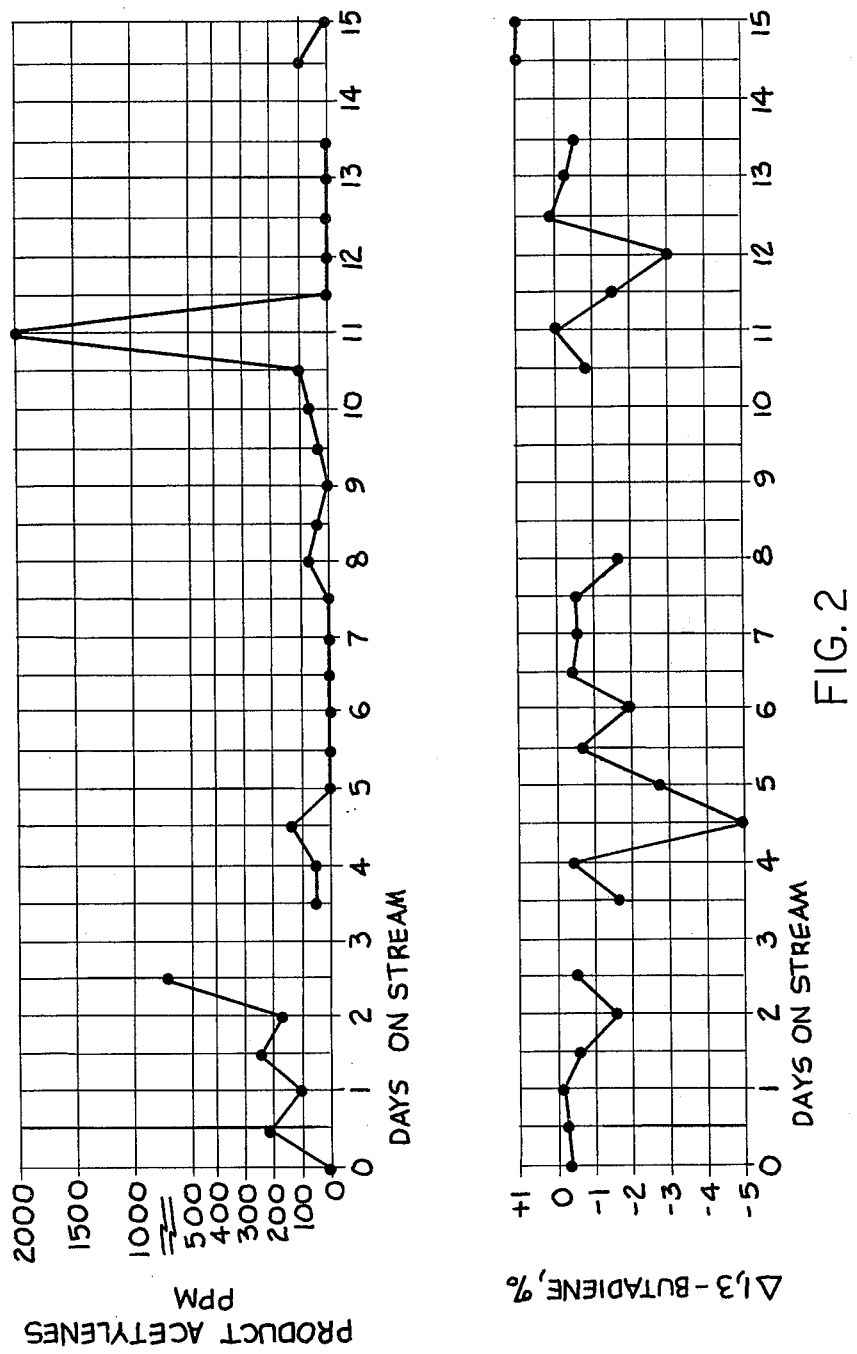
Figure 3:
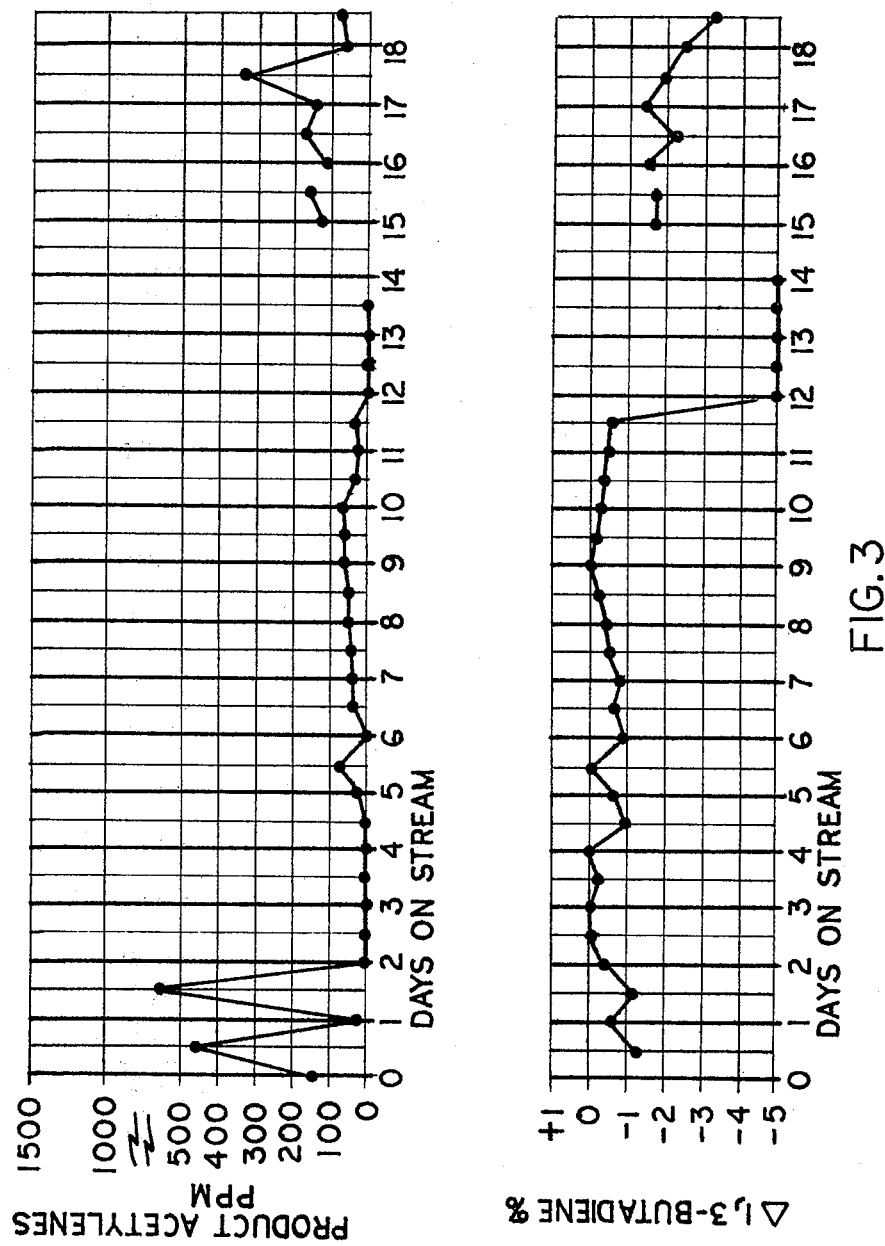
Figure 4:
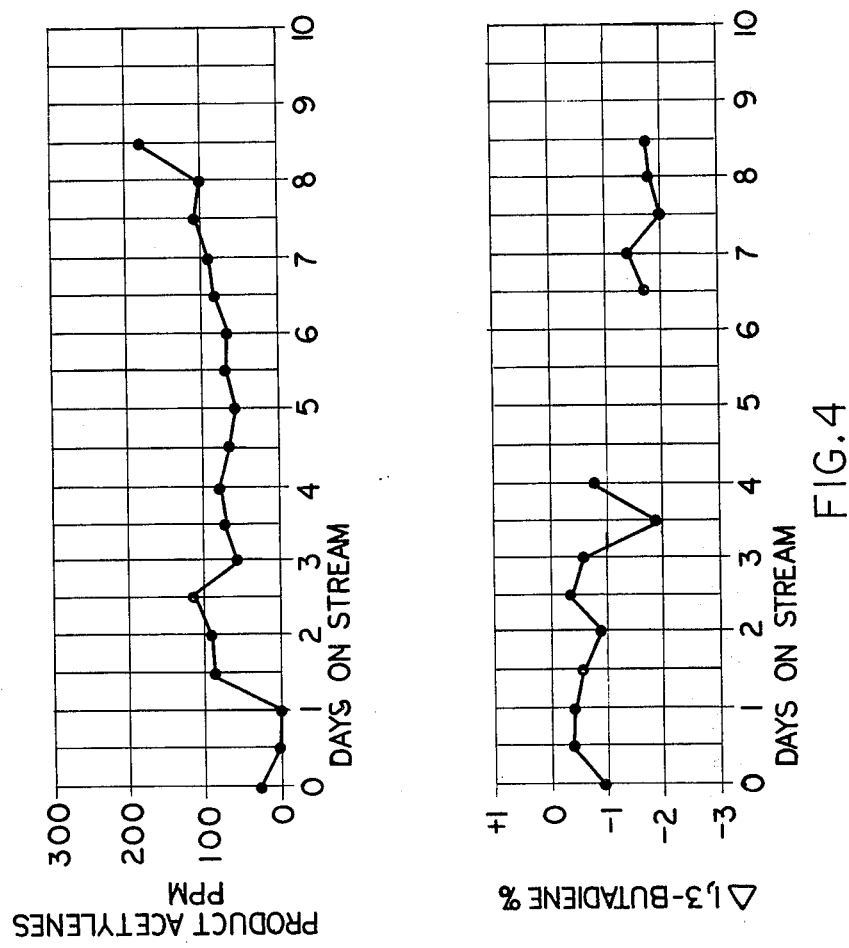
Figure 5:
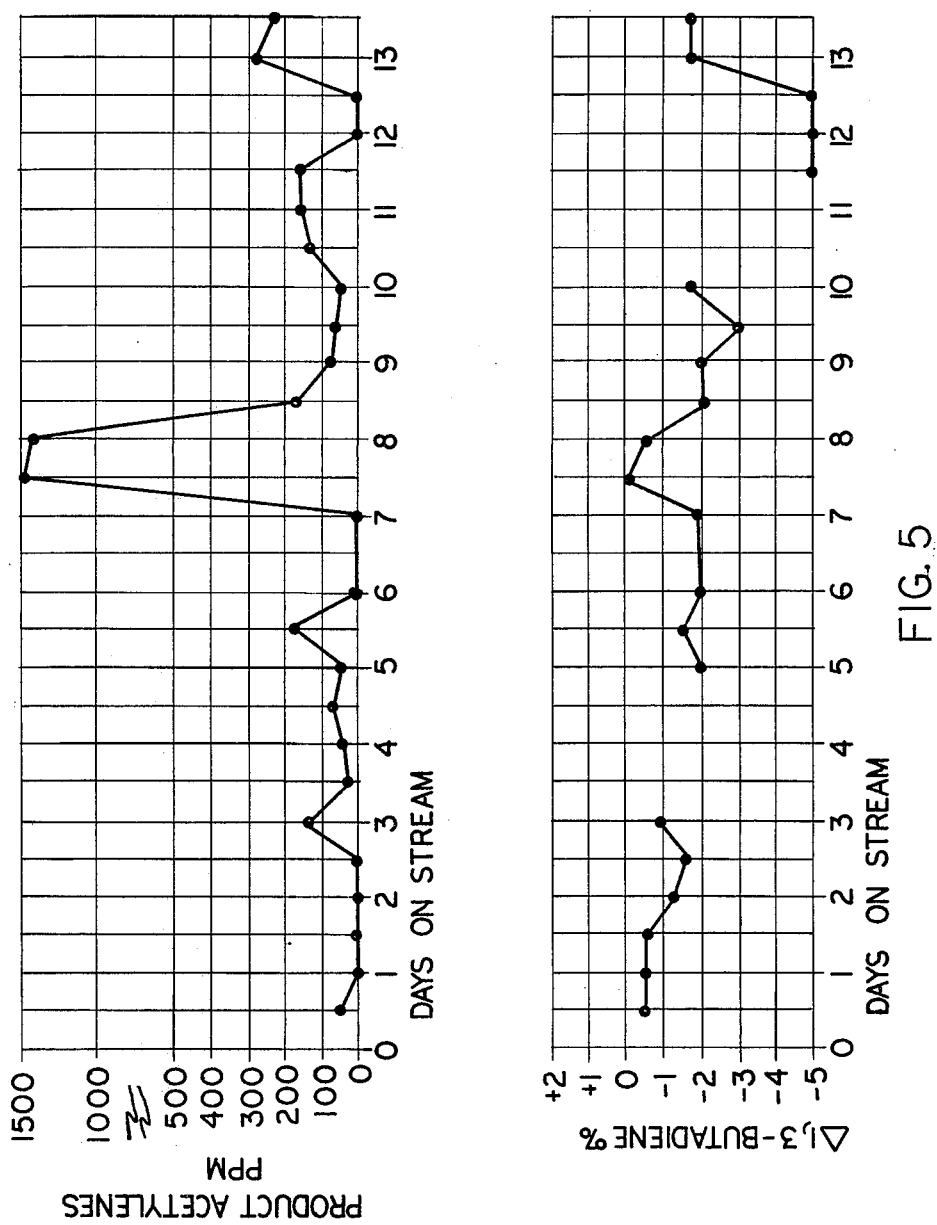
Figure 6:
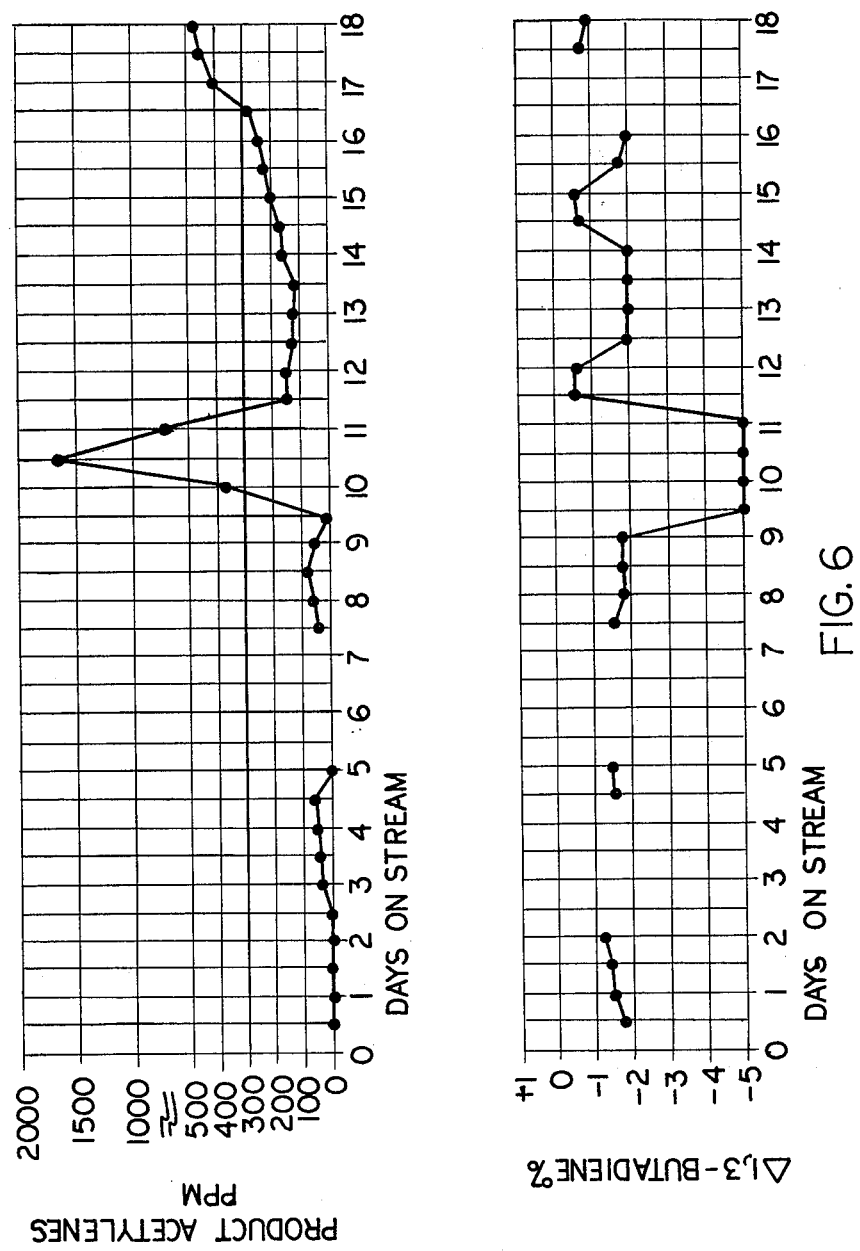

The results of two runs with regeneration are illustrated in FIG. 1 which shows that the product had an average of less than 80 ppm acetylenes, having hydrogenated over 8630 ppm of the acetylenes in the feed with less than 1% total butadiene loss based on the butadiene present in the feed.

EXAMPLE 2

To 400 grams of a catalyst support obtained from Calsicat Division, Mallinckrodt Chemical Works, identified as CALSICAT Type A having the following physical properties as ⅛" pellets:

| x-ray diffraction pattern matches Joint Committee on Powder Diffraction Standards #29-63 | |
|---|---|
| % Na$_2$O | 0.005 |
| % SiO$_2$ | 0.01 |
| % Fe$_2$O$_3$ | (<0.1) |
| % Sulfur | 0.01 |
| Surface area (m$^2$/g) | 200 |
| Pore volume (cc/g) | 0.50 |
| Bulk density (g/cc) | 0.8 | was added the following liquid mixture:

| | Grams | Parts By Weight |
|---|---|---|
| Cu(NO$_3$)$_2$.2½H$_2$O | 140 | 0.9164 |
| Ni(NO$_3$)$_2$.6H$_2$O | 4.75 | 0.0311 |
| Mn(NO$_3$)$_2$ 50% solution | 4 | 0.0262 |
| Co(NO$_3$)$_3$.6H$_2$O | 2 | 0.0131 |
| Cr(NO$_3$)$_3$.9H$_2$O | 2 | 0.0131 |
| HNO$_3$(conc.) | 1 | |
| AgNO$_3$ | 0.25 | 0.0016 |
| H$_2$O | ~50 | | in sufficient water of a pH of 6.5–7.5 to wet the surface of said support with stirring and heating, 50°–60° C., until the liquid was sorbed. Thereafter the wetted support was dried in an oven at 110° C. for 2 hours, then placed in a furnace at 400° C. at about noon and left overnight. The next morning the catalyst was removed from the furnace, cooled and packed in a reactor of like size and in the same manner as described in Example 1. The 72-day results of 5 cycles with regeneration as previously described are illustrated in FIGS. 2–6. The average α-acetylene content of the outlet product was less than 100 ppm (from 8000–10,000 ppm in feed) and a loss of butadiene of less than 1% of that in the feed.

EXAMPLE 3

In a similar manner as Example 2, 300 grams of a ⅛" pellet CALSICAT Type AA catalyst support was impregnated with a proportionate volume of the catalyst formulation, dried, packed in a similar reactor, reduced with H$_2$, and operated without regeneration for 57 days. The results of a two-month cycle, illustrated in FIG. 7, show an average of <50 ppm acetylene coming through during the first 35 days and <150 ppm acetylene coming through the next 22 days. The loss of butadiene during the entire 57 days was about 1%.

EXAMPLE 4

Likewise, a catalyst prepared on HARSHAW Al-3438T support was prepared and tested in a similar manner to the foregoing Examples. The results of six (6) days operation showed 200 ppm acetylenes (avg.) remaining in the treated liquids and a loss of about 2% butadiene.

EXAMPLE 5

Figure 8:
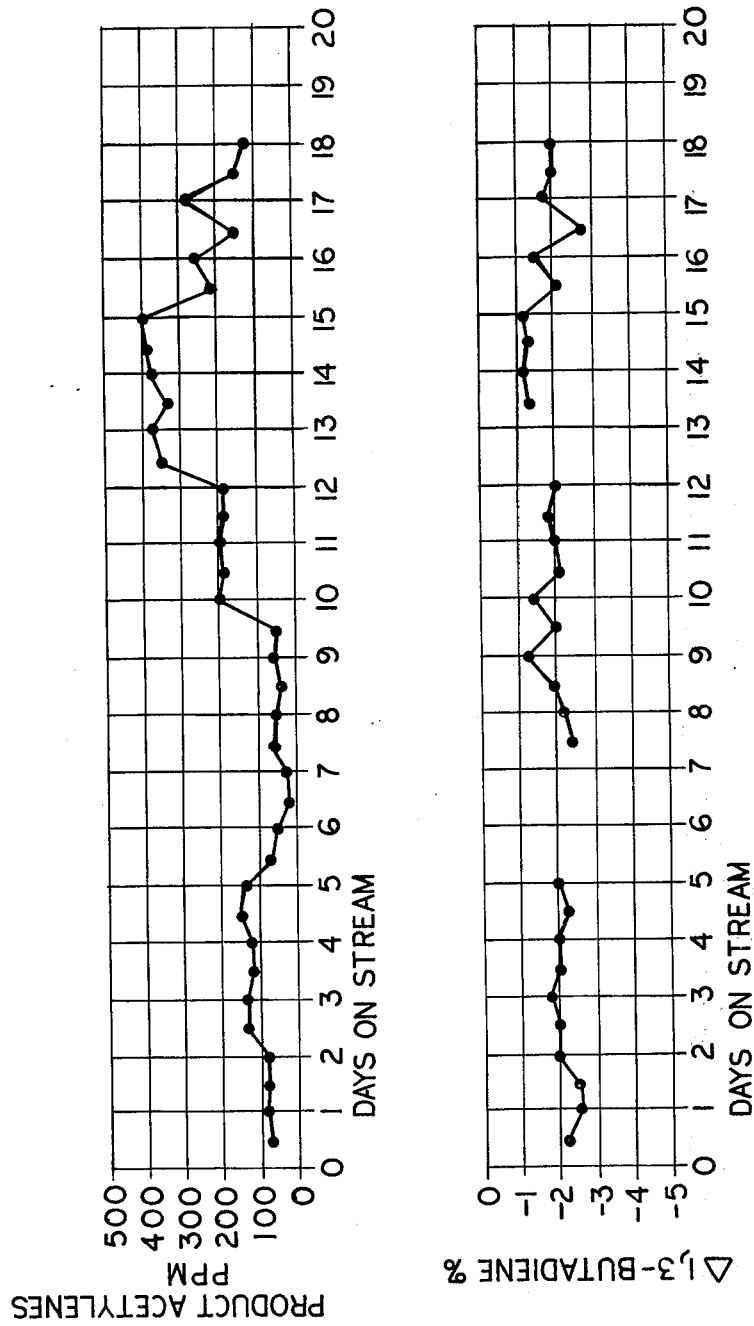
Figure 9:
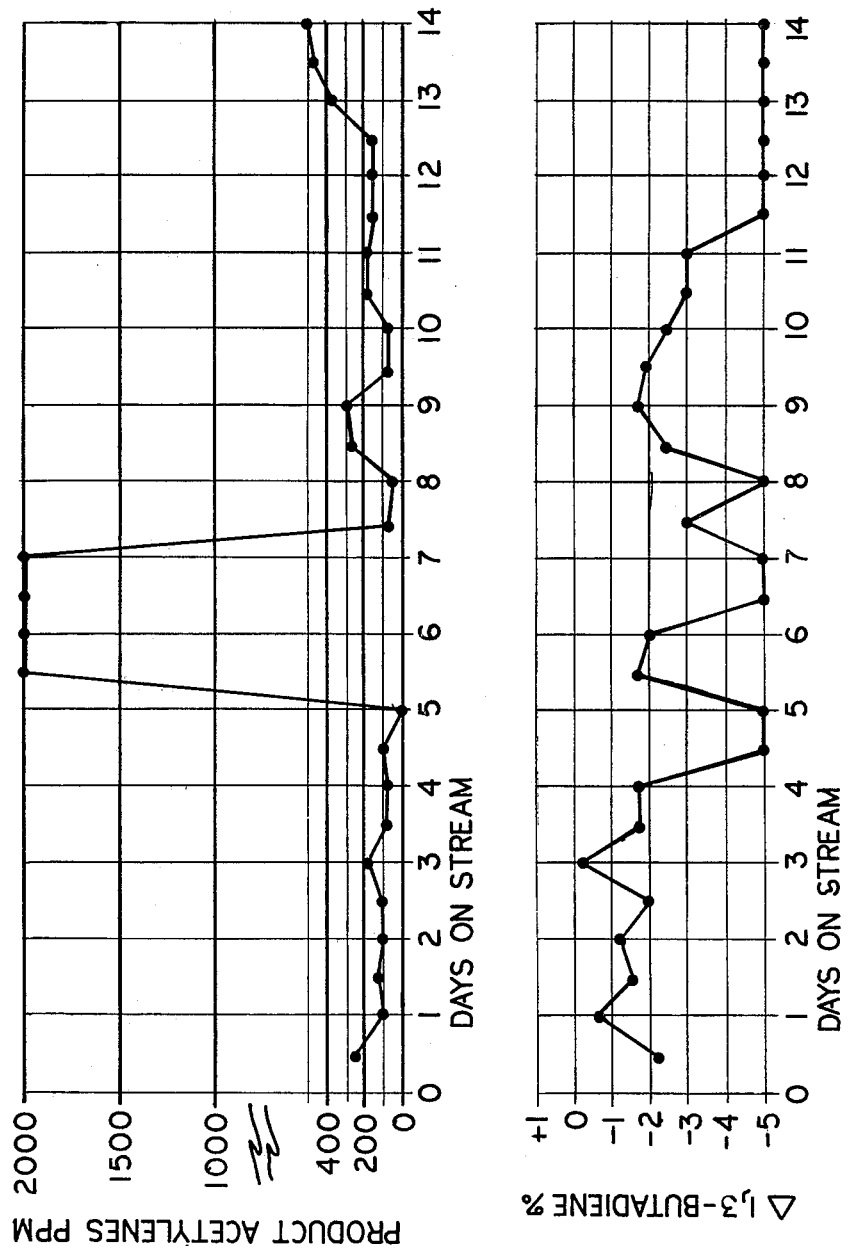

A NORTON SA6173 support was employed to prepare a catalyst and operated for a first cycle of 18 days in a test as afore described. Regeneration occurred on the 18th day. The processed liquids had an average of 200 ppm acetylenes and about a 1% loss in butadiene content on the initial run. The butadiene losses increased from 2 to 4% on the regenerated catalyst over a 15-day second cycle. The graphic daily results are shown in FIGS. 8 and 9.

In order to identify each support, the following table of physical properties is set forth.

Regeneration of the catalyst was carried out about every 14 to 21 days by heating to about 250° to 300° C. in the presence of nitrogen, then in the presence of air until an exotherm had passed through the bed, and then maintained on air for 2-4 hours, until no other exotherm wave was observed. The air was stopped and hydrogen of up to 5 volume percent in nitrogen passed through the bed until an exotherm moved through the bed. When no additional exotherm was observed within 2 to

|  | % $Na_2O$ | $SiO_2O$ % | % $Fe_2O_3$ | Surface Area $m^2/g$ | Pore Volume cc/g | Bulk Density g/cc | Sulfur |
|---|---|---|---|---|---|---|---|
| CALSICAT Type A | .005 | .01 | (<.01) | 200 | .50 | .80 | (.01) |
| HARSHAW Al-3438T | (.005) | (.01) | <.01 | 175 | .50 | .78 | (.01) |
| CATAPAL Type SB | .004 | .008 | .005 | 241 | .57 | .79 | .01 |
| CALSICAT Type AA | .07 | .12 |  | 215 | .70 | .63 | — |
| NORTON SA-6173 | .015 | .09 | .06 | 240 | .56 | .69 | — |
| REYNOLDS RA-1[1] | .35 | 66 ppm | 190 ppm | 213 | .18 | .88 | — |

[1]Conventional γ-AlOOH support.

Figure 10:
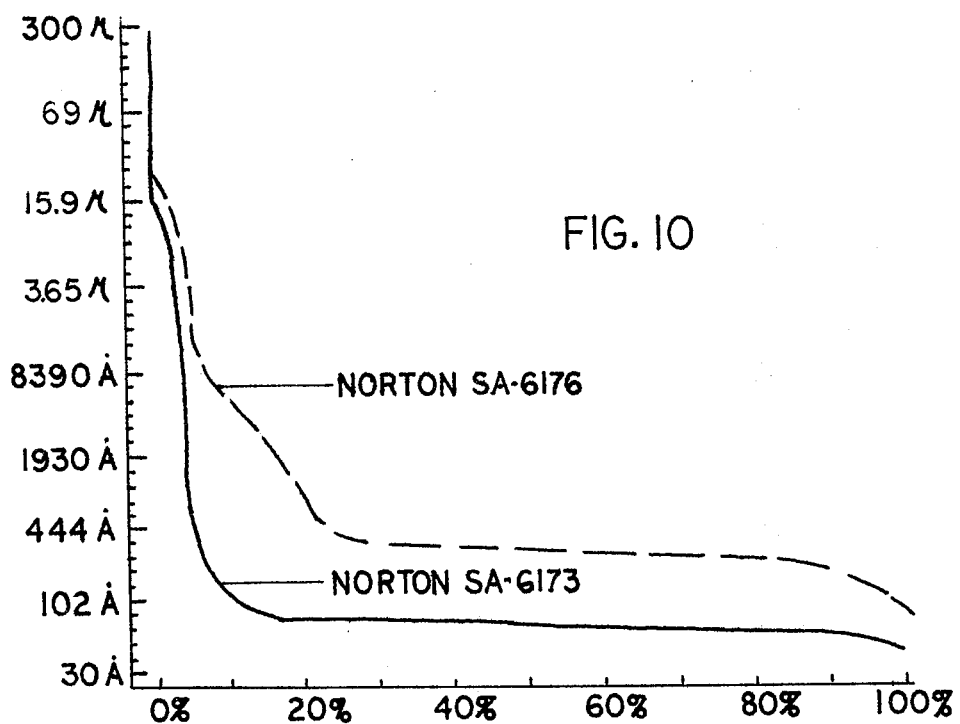
FIGS. 10, 11, 14 and 15 illustrate the pore size distribution of the several supports of the examples.
Figure 11:
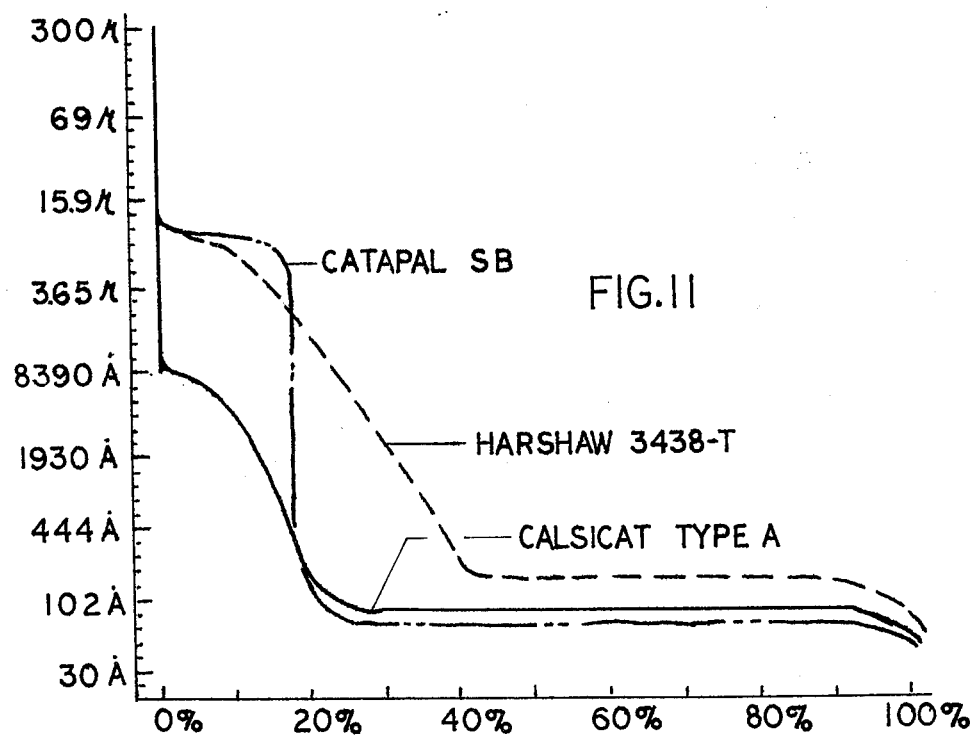

The pore distribution of each support is shown in the drawings, FIGS. 10 and 11.

EXAMPLE 6

For purposes of comparison, a catalyst having the exact composition as that applied in Example 1 was applied to a conventional gamma alumina (REYNOLDS RA-1 a γ-AlOOH) having a normal sodium content and pore size distribution. The results of 2 cycles, with regeneration in between after the 35th day of the first cycle, shows results illustrated in FIGS. 12 and 13; to wit: 100-200 acetylenes during the first cycle rising to 200-400 during the second cycle, with loss of butadiene in the 1 to 4% range in both cycles.

EXAMPLE 7

A catalyst prepared from a high purity Norton SA-6173 1/16" extrudates upon which copper and promoter metals were impregnated, was calcined at 400° C. for 8 hours. The proportions employed to prepare this catalyst were:

|  | grams |
|---|---|
| Norton SA-6173 1/16" | 4800 |
| $Cu(NO_3)_2 \cdot 2\frac{1}{2}H_2O$ | 1680 |
| $Ni(NO_3)_2 \cdot 6H_2O$ | 57 |
| $Mn(NO_3)_2$ 50% solution | 48 |
| $Co(NO_3)_2 \cdot 6H_2O$ | 24 |
| $Cr(NO_3)_3 \cdot 9H_2O$ | 24 |
| $HNO_3$ (conc.) | 85 |
| $AgNO_3$ | 3 |
| $H_2O$ | ~600 |

Figure 14:
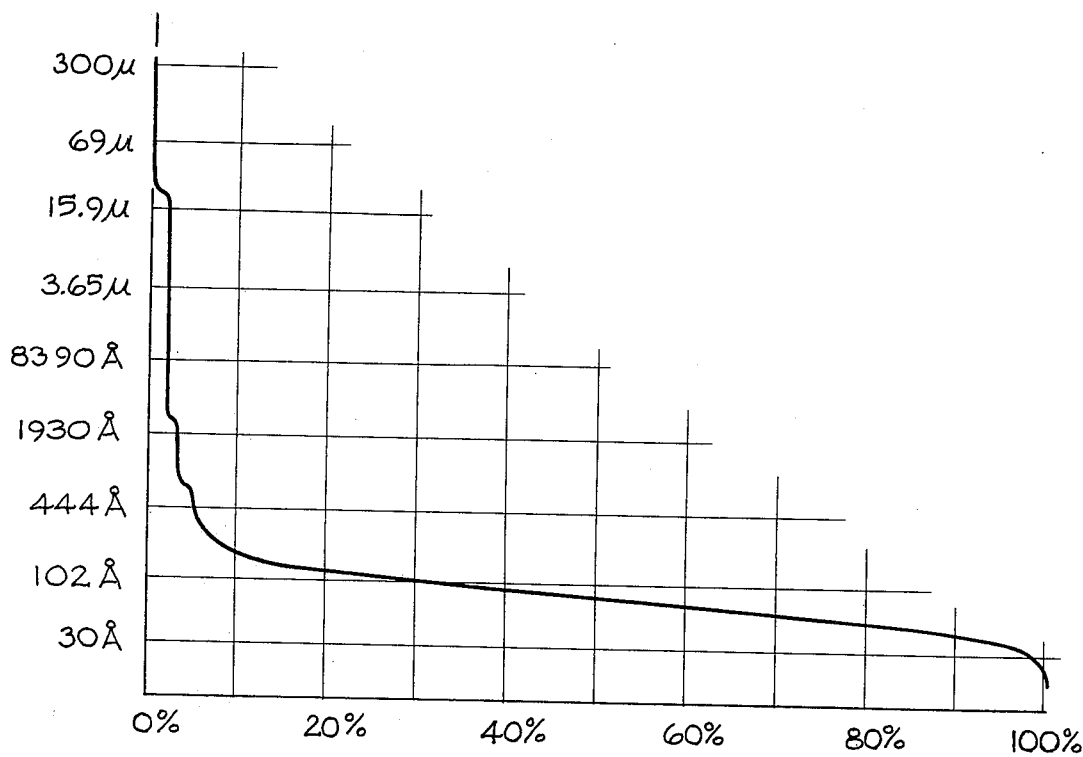
Figure 15:
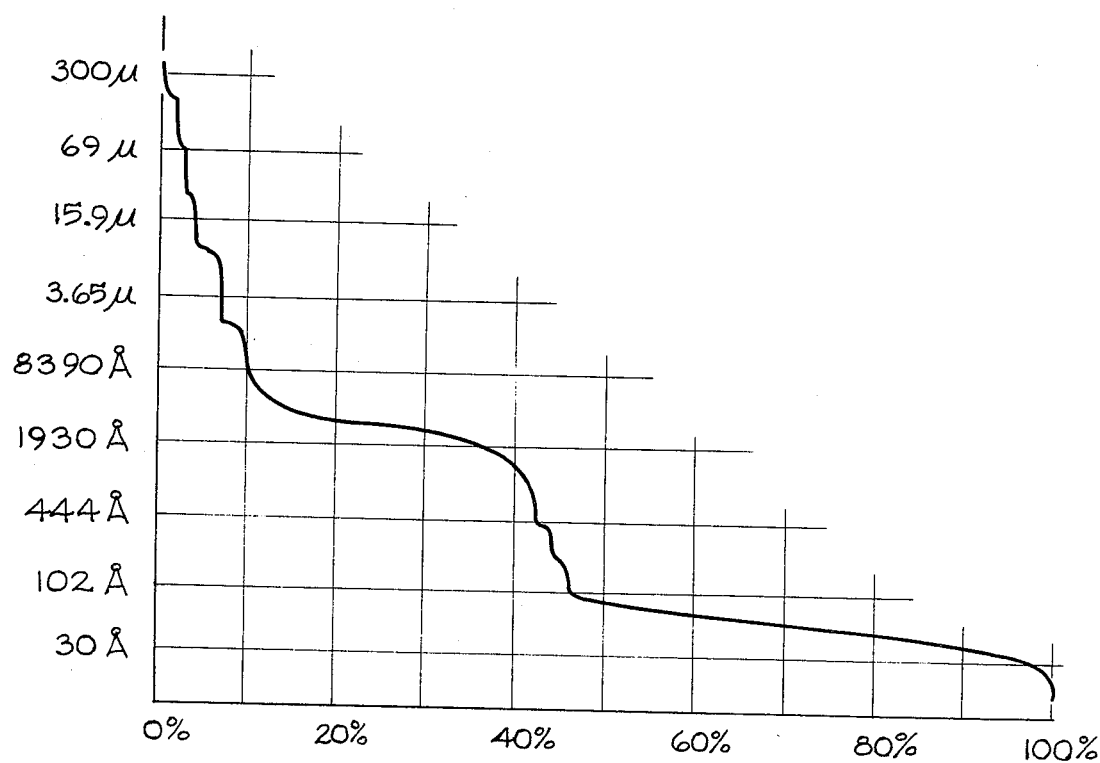

The calcined catalyst was loaded into a reactor, heated to 250° C. in the presence of nitrogen then reduced with up to 5 volume percent $H_2$ in nitrogen for about 12 hours. The reactor was cooled and liquid hydrocarbon was introduced into the reactor and catalyst bed. The reactor temperature was maintained between about 50° C. and 70° C. Hydrogen to acetylene molar ratio was maintained at about 3 to 4 throughout thirteen cycles. 4 hours on hydrogen, the bed was cooled and placed on line with hydrocarbon feed. The catalyst carrier had the initial pore volume distribution shown in FIG. 14 and a BET nitrogen surface area of 165 $m^2/g$. Following the twelfth cycle before regeneration the carrier had a pore volume distribution as shown in FIG. 15. The BET nitrogen surface area was 68 $m^2/g$.

The initial data of operation for the 13th cycle for 3 days was comparable to the initial 3 days operation of the first and subsequent cycles.

EXAMPLE 8

Figure 16:
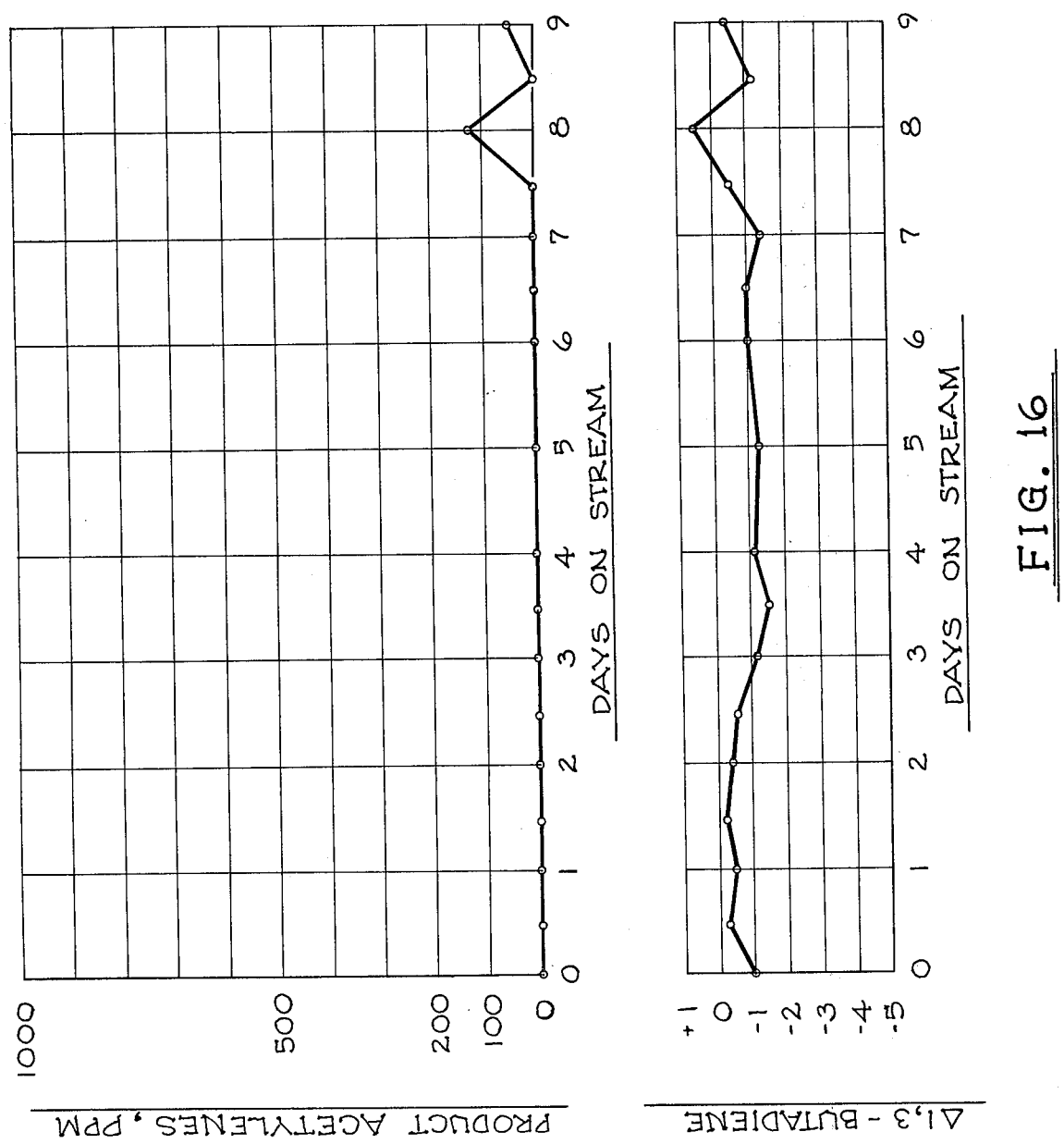
Figure 18:
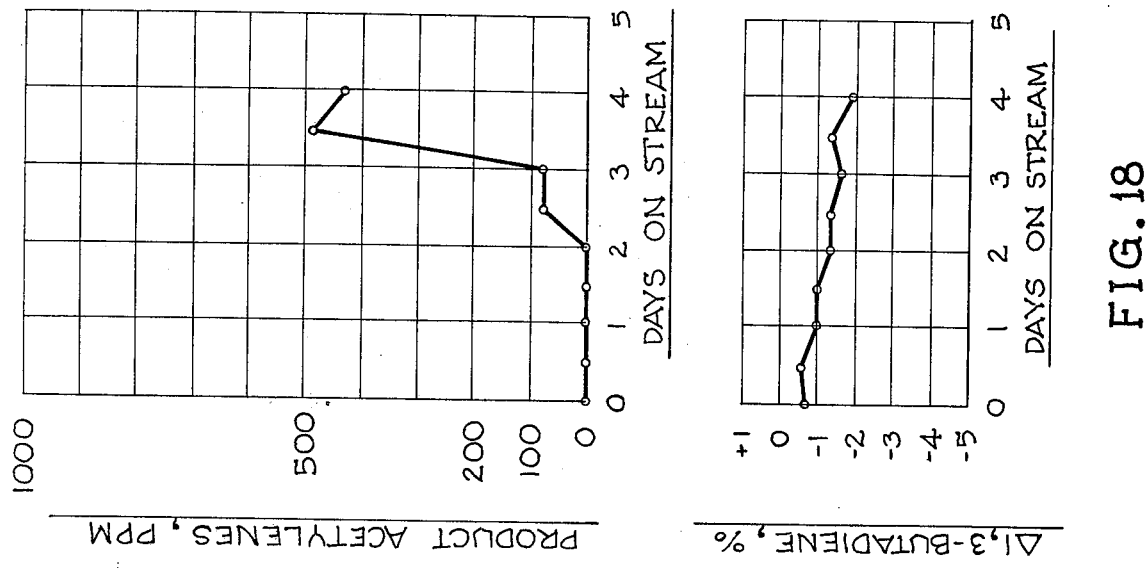
Figure 17:
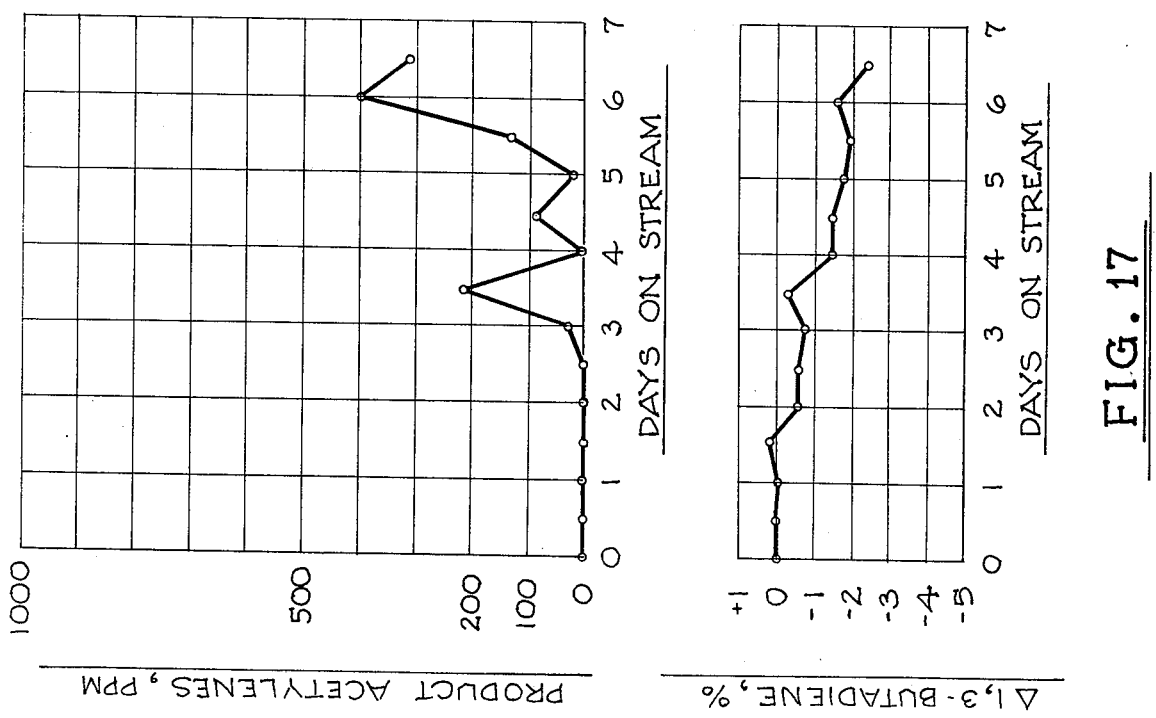
Figure 19:
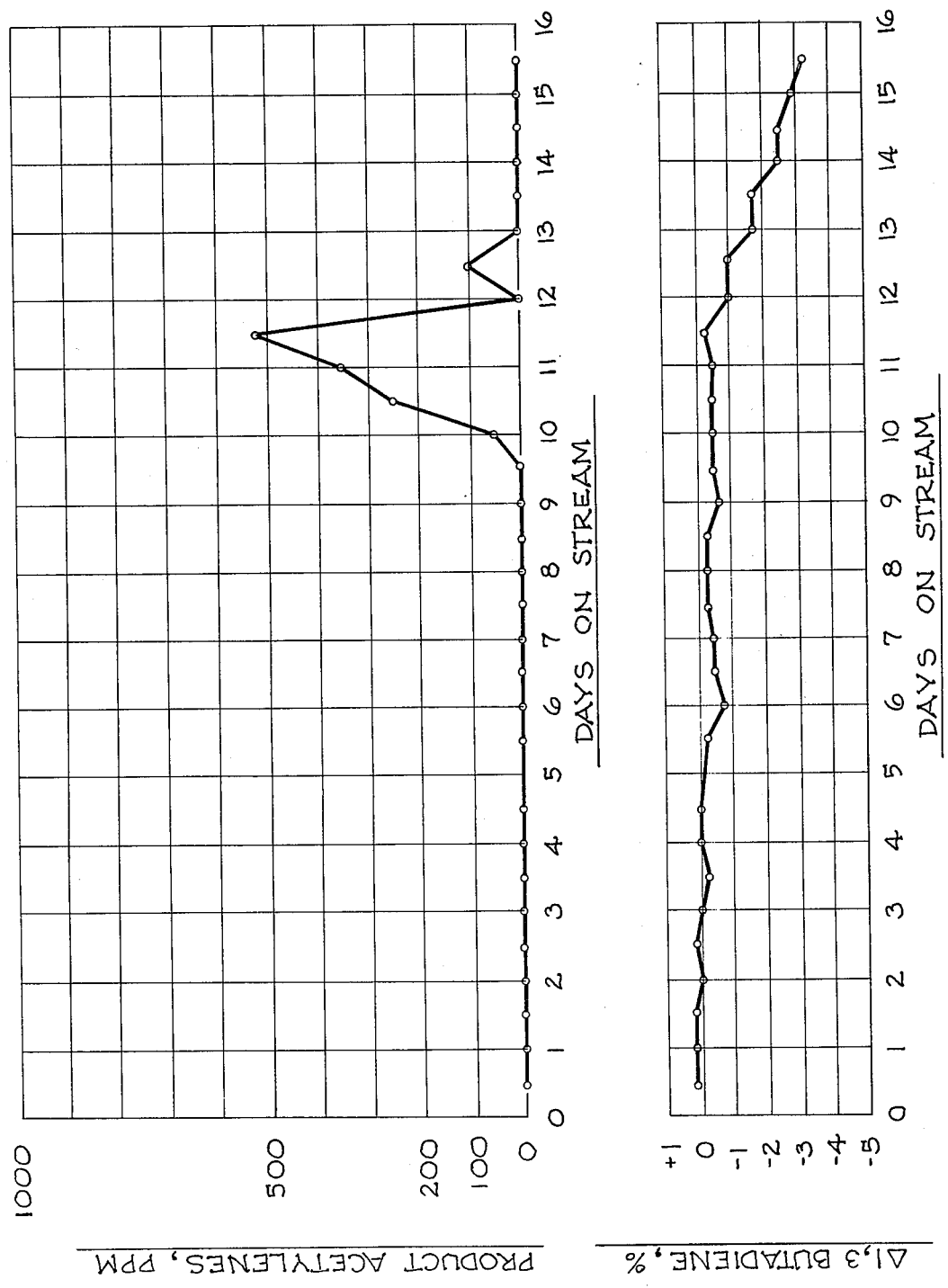
Figure 20:
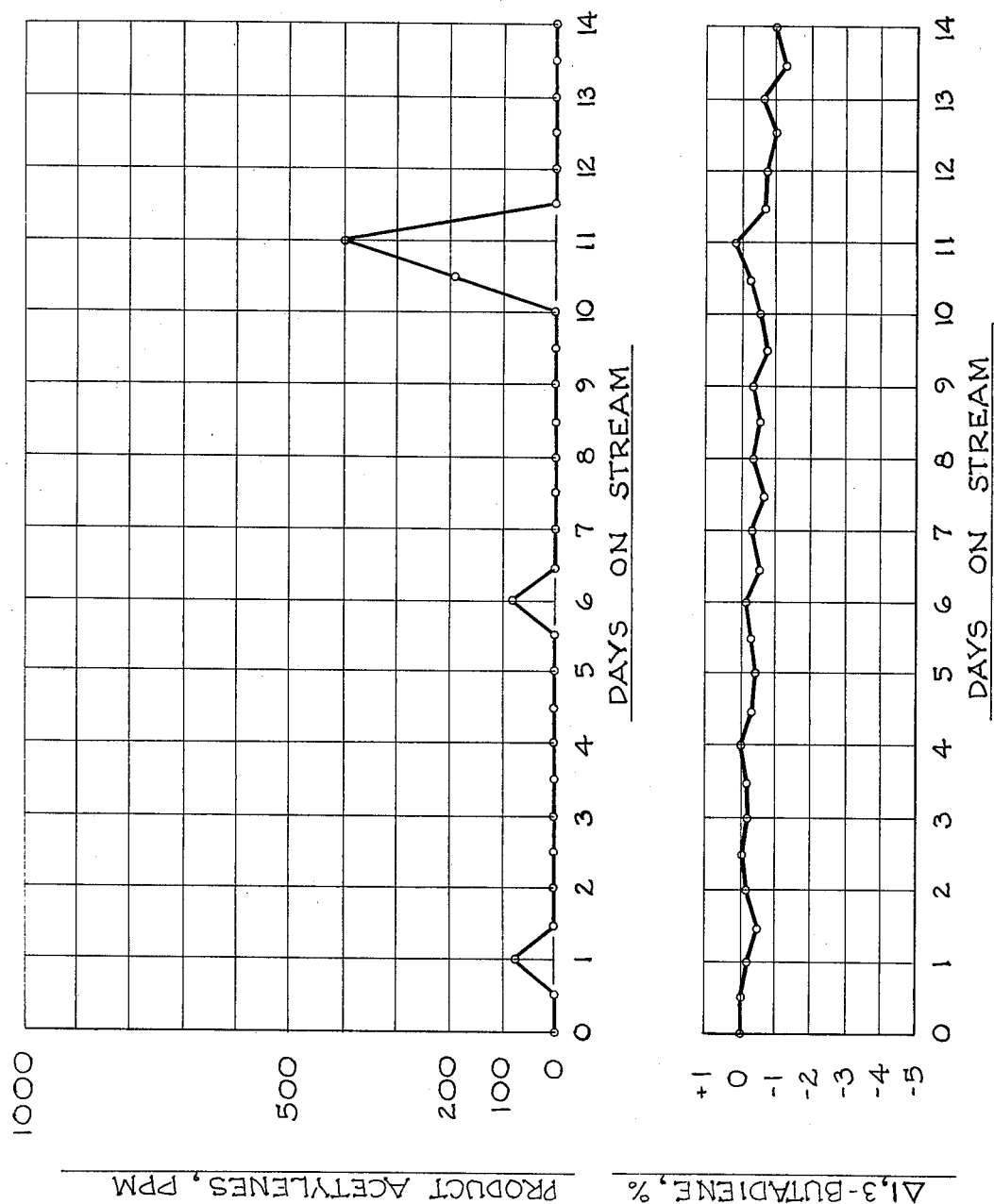

In evaluating the performance of the catalyst and its support in respect to materials of construction, it was found that the materials of construction for the reactor are critical if long, fourteen day, on stream cycles are desired. Thus when one employs a stainless steel containing nickel, the efficiencies of the catalysts of the present invention are somewhat reduced due to the necessity to regenerate the catalyst more often. This phenomenom is overcome when carbon steel is employed as the material of construction for the reactor. The effects of the presence of nickel even though only small amounts are possible at the internal surface of the reactor (wall effect) are clearly seen in FIGS. 16, 17, and 18, the 9th, 12th, and 13th cycles, in a 304 stainless steel reactor. The use of a carbon steel reactor illustrates the improved efficiency, i.e. longer run time between regeneration before the acetylenes are no longer effectually hydrogenated and is shown by comparing results of the three just mentioned runs, FIGS. 16, 17, and 18, with the results of the carbon steel reactor shown in FIGS. 19 and 20.

Figure 21:
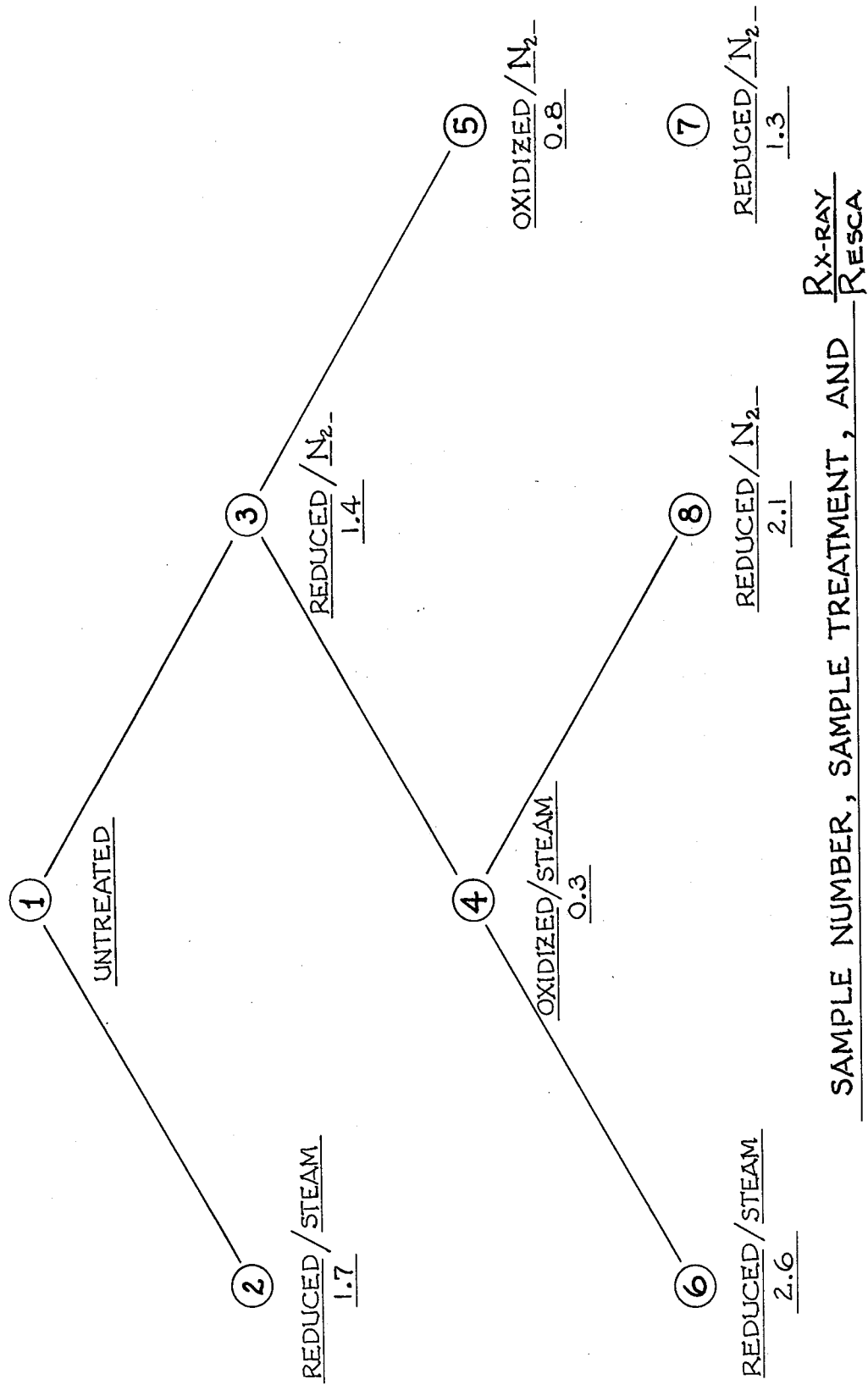

Another point which long run data establishes is that steam regeneration markedly reduces the life of a catalyst by a loss of surface copper and an increase in copper crystallite size following regeneration and/or oxidation of the catalyst. Results are illustrated in the following table. Samples were prepared in the sequence shown in FIG. 21.

COMPARISON OF STEAM AND N₂ DILUENTS DURING REGENERATION

| SAMPLE | DILUENT | FINAL OXIDATION STATE | % Cu++ | Cu°/γ-Al₂O₃ ESCA SMALL SURFACE SPECIES | Cu°/γ-Al₂O₃ X-RAY[1] LARGE BULK SPECIES | R x-ray R ESCA[2] LARGE TO SMALL CRYSTAL RATIO |
|---|---|---|---|---|---|---|
| 1 | — | Ox. | 100 | 1.58 | — | — |
| 2 | Steam | Red. | 5 | .50 | .86 | .7 |
| 3 | N₂ | Red. | 5 | .83 | 1.16 | 1.4 |
| 4 | Steam | Ox. | 73 | .97 | .25 | .3 |
| 5 | N₂ | Ox. | 29 | .89 | .75 | .3 |
| 6 | Steam | Red. | 1 | .27 | .69 | 2.6 |
| 7 | N₂ | Red. | 19 | .60 | .78 | 1.3 |
| 8 | N₂ | Red. | 7 | .54 | 1.13 | 2.1 |

[1] Total area for ESCA scan of the Cu 2p3/2 peak to total area per ESCA scan of the aluminum 2s peak was taken as amount of small copper particles present in the catalyst.
[2] The ratio of the height of the copper 2.09 Å peak by x-ray diffraction to the γ-Al₂O₃ 1.40 Å peak of x-ray diffraction was calculated as a measure of the large copper crystallites present. Ratio of x-ray ratio to ESCA ratio was calculated as ratio of large to small copper crystallites.

I claim:

1. A catalyst for removing α-acetylenes from liquid hydrocarbon streams consisting essentially of a mixture of finely divided copper metal and minor amounts of at least one polyvalent activator metal selected from the group consisting of silver, platinum, palladium, manganese, cobalt, nickel, chromium and molybdenum, dispersed on an aluminum oxide support, said support being a gamma alumina as defined by the Joint Committee on Powder Diffraction Standards, #29-63, of high purity having a surface area of between about 68 and about 350 square meters per gram, and 90 to 60 percent of the pores have a pore diameter between about 40 Å and 120 Å and not more than 25 percent nor less than 2 percent have a pore diameter between 1000 Å to 10,000 Å, a silicone content as SiO₂ of less than about 0.15 weight %, a sodium content as Na₂O of less than about 0.15 weight %, a sulfur content less than about 0.01 weight % and an iron content as Fe₂O₃ of less than about 0.06 weight %, said gamma alumina may contain up to 35% by weight of alpha alumina.

2. A catalyst for removing α-acetylenes from liquid hydrocarbon streams consisting essentially of a support having thereon a mixture of finely divided copper metal and minor amounts of at least one polyvalent activator metal selected from the group consisting of silver, platinum, palladium, manganese, cobalt, nickel, chromium and molybdenum, said support being a substantially high purity gamma alumina as defined by the Joint Committee on Powder Diffraction Standards #29-63, having a surface area of at least about 68 to about 350 square meters per gram, and 90 to 60 percent of the pores have a pore diameter between about 40 Å and 120 Å and not more than 25 percent nor less than 2 percent have a pore diameter between 1000 Å to 10,000 Å, and having a sodium content less than about 0.15% and SiO₂ being less than 0.15% and which may contain up to 35% by weight of alpha alumina.

3. A catalyst for removing α-acetylenes from liquid hydrocarbon streams consisting essentially of a support having thereon a mixture of finely divided copper metal and minor amounts of at least one polyvalent activator metal selected from the group consisting of silver, platinum, palladium, manganese, cobalt, nickel, chromium and molybdenum, said support being a substantially high purity gamma alumina as defined by the Joint Committee on Powder Diffraction Standards #29-63, having a surface area of at least about 68 to about 350 square meters per gram, and 90 to 60 percent of the pores have a pore diameter between about 40 Å and 120 Å and not more than 25 percent nor less than 2 percent have a pore diameter between 1000 Å to 10,000 Å, and having a sodium content less than about 0.15% and SiO₂ being less than 0.15%, and which may contain up to 35% by weight of alpha alumina, said copper metal being present in from about 3 to 13 weight percent of the support and said combined weight of said activator metals being from 0 to about 15 percent of the copper metal.

4. A catalyst for removing α-acetylenes from liquid hydrocarbon streams consisting essentially of a support having thereon a mixture of finely divided copper metal and minor amounts of at least one polyvalent activator metal selected from the group consisting of silver, manganese, cobalt, nickel, and chromium, said support being a substantially high purity gamma alumina as defined by the Joint Committee on Powder Diffraction Standards #29-63, having a surface area of at least about 68 to about 350 square meters per gram, and 90 to 60 percent of the pores have a pore diameter between about 40 Å and 120 Å and not more than 25 percent nor less than 2 percent have a pore diameter between 1000 Å to 10,000 Å, and having a sodium content less than about 0.15% and SiO₂ being less than 0.15% and which may contain up to 35% by weight of alpha alumina, said copper metal being present in from about 3 to 13 weight percent of the support and said combined weight of said activator metals being from 0 to about 15 percent of the copper metal, said catalytic metal being applied to said support by reduction of the metal nitrate salts of an aqueous solution composed of

| Cu(NO₃)₂.2½H₂O | 9135 parts by weight |
|---|---|
| Ni(NO₃)₂.6H₂O | .0323 |
| Mn(NO₃)₂ 50% active | .0250 |
| AgNO₃ | .0016 |
| Cr(NO₃)₃.9H₂O | .0137 |
| Co(NO₃)₂.6H₂O | .0137 | in sufficient water of a pH of 6.5-7.5 to wet the surface of said support.

5. A catalyst for removing α-acetylenes from liquid hydrocarbon streams consisting essentially of a support having thereon a mixture of finely divided copper metal and minor amounts of at least one polyvalent activator metal selected from the group consisting of silver, manganese, cobalt, nickel, and chromium, said support being a substantially high purity gamma alumina as defined by the Joint Committee on Powder Diffraction Standards #29-63, having a surface area of at least about 68 to about 350 square meters per gram, and 90 to 60 percent of the pores have a pore diameter between about 40 Å and 120 Å and not more than 25 percent nor less than 2 percent have a pore diameter between 1000 Å to 10,000 Å, and having a sodium content less than about 0.15% and $SiO_2$ being less than 0.15% and which may contain up to 35% by weight of alpha alumina, said copper metal being present in from about 3 to 13 weight percent of the support and said combined weight of said activator metals being from 0 to about 15 percent of the copper metal, said catalytic metal being applied to said support by reduction of the metal nitrate salts of an aqueous solution composed of

| | |
|---|---|
| $Cu(NO_3)_2 \cdot 2\frac{1}{2}H_2O$ | .9164 parts by weight |
| $Ni(NO_3)_2 \cdot 6H_2O$ | .0311 |
| $Mn(NO_3)_2$ 50% active | .0262 |
| $AgNO_3$ | .0016 |
| $Cr(NO_3)_3 \cdot 9H_2O$ | .0131 |
| $Co(NO_3)_2 \cdot 6H_2O$ | .0131 | in sufficient water of a pH of 6.5–7.5 to wet the surface of said support.

6. In a process for the removal of α-acetylenes from liquid hydrocarbon streams containing the same and 1,3-butadiene by contacting the stream with a catalyst comprised of copper metal and one or more activator metals selected from the group consisting of silver, platinum, palladium, manganese, cobalt, nickel, chromium and molybdenum dispersed on an alumina support the improvement which comprises employing the catalyst of claim 1.

* * * * *